US012292450B2

(12) United States Patent
Kimura et al.

(10) Patent No.: US 12,292,450 B2
(45) Date of Patent: May 6, 2025

(54) EXAMINATION METHOD FOR DEMENTIA OR RISK THEREOF

(71) Applicant: KAO CORPORATION, Tokyo (JP)

(72) Inventors: Ren Kimura, Haga-gun (JP); Hisashi Tsujimura, Utsunomiya (JP); Masaru Tsuchiya, Saitama (JP); Satoko Soga, Sumida-ku (JP); Noriyasu Ota, Shimotsuke (JP); Hunkyung Kim, Asaka (JP)

(73) Assignee: KAO CORPORATION, Tokyo (JP)

( * ) Notice: Subject to any disclaimer, the term of this patent is extended or adjusted under 35 U.S.C. 154(b) by 748 days.

(21) Appl. No.: 17/609,945

(22) PCT Filed: May 19, 2020

(86) PCT No.: PCT/JP2020/019780
§ 371 (c)(1),
(2) Date: Nov. 9, 2021

(87) PCT Pub. No.: WO2020/235559
PCT Pub. Date: Nov. 26, 2020

(65) Prior Publication Data
US 2022/0206016 A1    Jun. 30, 2022

(30) Foreign Application Priority Data

May 20, 2019 (JP) .................................. 2019-094474
Jan. 8, 2020 (JP) .................................. 2020-001652

(51) Int. Cl.
*G01N 33/68* (2006.01)

(52) U.S. Cl.
CPC ..... *G01N 33/6896* (2013.01); *G01N 33/6812* (2013.01); *G01N 33/6848* (2013.01); *G01N 2800/2814* (2013.01)

(58) Field of Classification Search
None
See application file for complete search history.

(56) References Cited

U.S. PATENT DOCUMENTS

| 2015/0079623 | A1 | 3/2015 | Hamase et al. |
| 2016/0178642 | A1 | 6/2016 | Uchida et al. |
| 2017/0239215 | A1 | 8/2017 | Salama |
| 2018/0217113 | A1 | 8/2018 | Harada et al. |

(Continued)

FOREIGN PATENT DOCUMENTS

| CN | 104246497 A | 12/2014 |
| CN | 109709235 A | 5/2019 |

(Continued)

OTHER PUBLICATIONS

International Search Report mailed on Aug. 25, 2020 in PCT/JP2020/019780 filed on May 19, 2020 (2 pages).

(Continued)

*Primary Examiner* — Xiaoyun R Xu
(74) *Attorney, Agent, or Firm* — Oblon, McClelland, Maier & Neustadt, L.L.P.

(57) ABSTRACT

Provided is an accurate, minimally invasive method for diagnosing dementia or mild cognitive impairment. The method for examining the likelihood of mild cognitive impairment or dementia, or the risk of dementia includes the steps of: measuring the amount of stereoisomers of proline in the biological sample collected from a subject; and comparing the level of D-proline with a reference value.

8 Claims, 6 Drawing Sheets

(56) References Cited

U.S. PATENT DOCUMENTS

| | | |
|---|---|---|
| 2019/0025320 A1 | 1/2019 | Hamase et al. |
| 2019/0277862 A1 | 9/2019 | Ikeuchi et al. |
| 2020/0200767 A1 | 6/2020 | Uchida et al. |

FOREIGN PATENT DOCUMENTS

| | | |
|---|---|---|
| EP | 2 950 102 A1 | 12/2015 |
| JP | 6214016 B2 | 9/2017 |
| JP | 2017-223711 A | 12/2017 |
| JP | 2018-100906 A | 6/2018 |
| JP | 2021-128132 A | 9/2021 |
| JP | 2022-142070 A | 9/2022 |
| WO | WO 2007/133076 A2 | 11/2007 |
| WO | WO 2014/207888 A1 | 12/2014 |
| WO | WO 2018/008764 A1 | 1/2018 |
| WO | WO 2019/012667 A1 | 1/2019 |

OTHER PUBLICATIONS

Madeira et al., "D-serine levels in Alzheimer's disease: implications for novel biomarker development", Transl Psychiatry, 2015, 5, e561; doi:10.1038/tp.2015.52, pp. 1-9.

Samakashvili et al., "Analysis of chiral amino acids in cerebrospinal fluid samples linked to different stages of Alzheimer disease", Electrophoresis, 2011, 32, pp. 2757-2764.

Yoshimitsu Kiriyama, et al., "D-Amino Acids in the Nervous and Endocrine Systems," Scientifica, vol. 2016, Article ID 6494621, 10 pages.

Y. Nagata, et al., "The presence of free D-serine, D-alanine and D-proline in human plasma," Experientia, vol. 48, 1992, pp. 986-988.

Květa Kalíková, et al., "Enantiomeric Ratio of Amino Acids as a Tool for Determination of Aging and Disease Diagnostics by Chromatographic Measurement," Separations, vol. 3, No. 30, 2016, 18 pages.

Antimo D'Aniello, et al., "Regional decreases of free D-aspartate levels in Alzheimer's disease," Neuroscience Letters, vol. 250, 1998, pp. 131-134.

George H. Fisher, et al., "Free D-Aspartate and D-Alanine in Normal and Alzheimer Brain." Brain Research Bulletin, vol. 26, 1991, pp. 983-985.

Christian Czech, et al., "Metabolite Profiling of Alzheimer's Disease Cerebrospinal Fluid," PloS ONE, vol. 7, Issue 2, e31501, Feb. 2012, pp. 1-10.

Kazuhiko Uchida, et al., "Amyloid-β sequester proteins as blood-based biomarkers of cognitive decline," Alzheimer's & Dementia: Diagnosis, Assessment & Disease Monitoring, vol. 1, 2015, pp. 270-280.

Extended European Search Report issued Feb. 17, 2023 in European Patent Application No. 20810358.0, 8 pages.

Xing et al., "Simultaneous determination of 18 D-amino acids in rat plasma by an ultrahigh-performance liquid chromatography-tandem mass spectrometry method: application to explore the potential relationship between Alzheimer's disease and D-amino acid level alterations", Analytical and Bioanalytical Chemistry, vol. 408, No. 1, Oct. 24, 2015, pp. 141-150 (total 10 Pages), XP035867604.

Li et al., "Development of an UPLC-MS/MS method for simultaneous quantitation of 11 d-amino acids in different regions of rat brain: Application to a study on the associations of D-amino acid concentration changes and Alzheimer's disease", Journal of chromatography, vol. 1058, May 11, 2017, pp. 40-46 (total 7 pages), XP085042389.

Kimura, et al., "Development of a cognitive function marker based on D-amino acid proportions using new chiral tandem LC-MS/MS systems", Scientific Reports, vol. 10, No. 1, Jan. 21, 2020, 12 pages, XP093021980, Retrieved from the internet: URL: https://www.nature.com/articles/s41598-020-57878-y.

Zuojun, et al., "Study on the Relationship Between Chiral Amino Acids and D-Amino Acids Separation by High Performance Capillary Electrophoresis and Presenile Dementia (Review)", Chinese Journal of Neuroimmunology and Neurology, vol. 5, No. 2, Jun. 30, 1998, pp. 125-128 (with unedited computer-generated English translation).

Kori, et al., "Metabolic Biomarkers and Neurodegeneration: A Pathway Enrichment Analysis of Alzheimer's Disease, Parkinson's Disease, and Amyotrophic Lateral Sclerosis", Journal of Integrative Biology, vol. 20, No. 11, Dec. 31, 2016, pp. 645-661.

EXAMINATION METHOD FOR DEMENTIA OR RISK THEREOF

FIELD OF THE INVENTION

The present invention relates to a method for examining mild cognitive impairment or dementia, or a risk thereof, using D-amino acids.

BACKGROUND OF THE INVENTION

Dementia is a type of cognitive impairment and is a state in which the intelligence once normally developed is irreversibly degraded due to an acquired organic disorder of the brain. There are various types of dementia such as Alzheimer's disease, cerebrovascular dementia, Lewy body dementia, and frontotemporal (pick type) dementia, and their causes are also different.

Currently, for the diagnosis of dementia, methods of measuring amyloid β and tau protein in blood have also been reported in recent years, in addition to cognitive function test, genetic test, metabolome measurement of amyloid β and tau protein in cerebrospinal fluid, brain imaging, and behavioral evaluation. However, these are not always practical in view of accuracy and cost.

In recent years, with the importance of early diagnosis of dementia, the state of mild cognitive impairment (MCI), which means the precursor state of dementia, has attracted attention. It is important to accurately diagnose dementia, including mild cognitive impairment which is the earliest stage, and it is necessary to develop biomarkers.

Meanwhile, all amino acids other than glycine have two types of stereoisomers, D-form and L-form. Since L-amino acids are constituents of proteins of living organisms, and the amino acids contained in proteins are L-amino acids, in principle, L-form amino acids have been considered to be mainly involved in the physiological activity of higher animals. However, with the improvement of separability and sensitivity due to recent progresses in analytical technology, the existence and role of D-amino acids in mammals including humans have been clarified. Recently, it has been reported that the amounts of D-amino acids and L-amino acids in biological materials in healthy persons maintain a certain balance, and there is an imbalance between D-amino acids and L-amino acids in some diseases (Patent Literature 1). In this literature, the relationship between Alzheimer's disease and D-amino acids in blood is also studied, and it is suggested that the balance of D-serine, D-alanine, D-methionine, D-leucine, D-aspartic acid, D-phenylalanine, or D-allo-isoleucine changes in patients with Alzheimer's disease. However, a unified view regarding D-serine has not been obtained; for example, there mixedly exist a report suggesting that D-serine in cerebrospinal fluid can be a biomarker for early diagnosis of Alzheimer's disease (Non Patent Literature 1) and a report that no correlation between D-serine in cerebrospinal fluid and Alzheimer's disease or mild cognitive impairment is observed (Non Patent Literature 2).

Patent Literature 1: JP-A-2017-223711
Non Patent Literature 1: C Madeira, M V Lourenco, C Vargas-Lopes, C K Suemoto, C O Brandao, T Reis, R E P Leite, J Laks, W Jacob-Filho, C A Pasqualucci, L T Grinberg, S T Ferreira and R Panizzutti, Transl Psychiatry. 2015; 5:1-9. doi:10.1038/tp.2015.52. Epub 2015 May 5.
Non Patent Literature 2: Shorena Samakashvili, Clara Ibanez, Carolina Simo, Francisco J. Gil-Bea, Bengt Winblad, Angel Cedazo-Minguez, Alejandro Cifuentes, Electrophoresis. 2011; 32(19):2757-2764. Doi: 10.1002/elps.201100139. Epub 2011 Aug. 29.

SUMMARY OF THE INVENTION

The present invention relates to 1) and 2) below.
1) A method for examining mild cognitive impairment or dementia, or a risk thereof, comprising the steps of: measuring the amount of stereoisomers of proline in a biological sample collected from a subject; and comparing the level of D-proline with a reference value.
2) An apparatus for performing the examination method of 1) above to examine mild cognitive impairment or dementia, or a risk thereof, comprising: a means for measuring the amount of stereoisomers of an amino acid in the biological sample; a means for comparing the level of D-amino acid with a reference value; and a means for outputting the condition of the subject or risk information thereof based on the comparison.

DETAILED DESCRIPTION OF THE INVENTION

Figure 1:
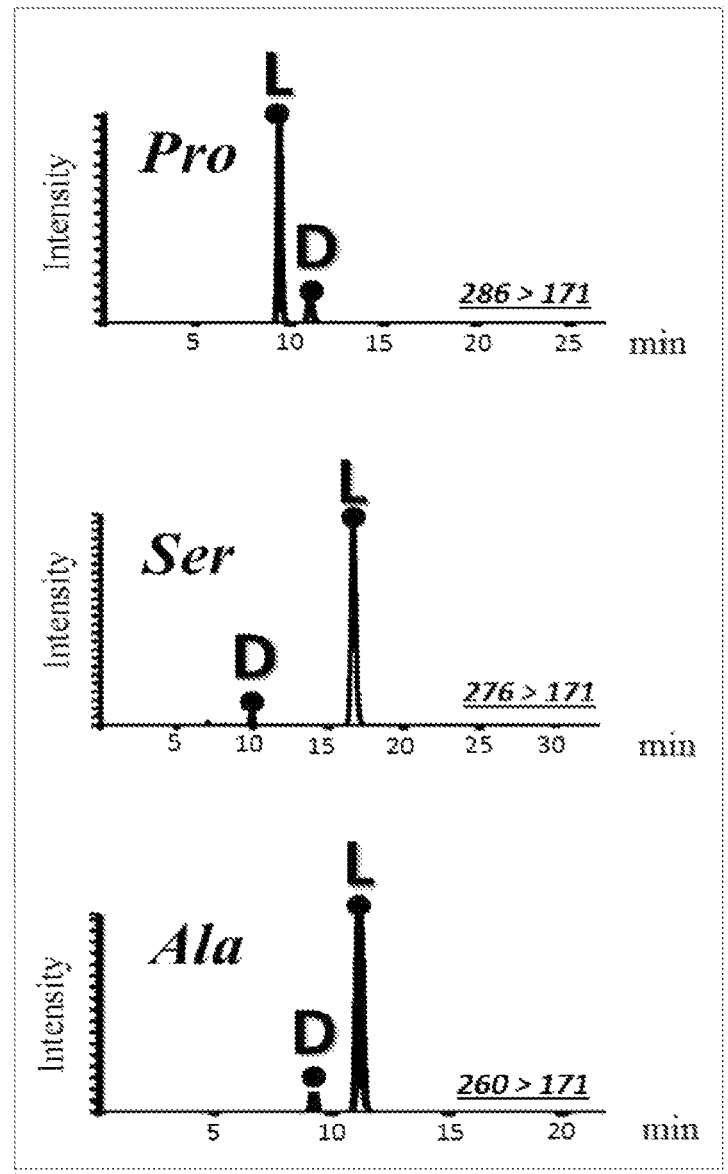
FIG. 1 includes chromatograms of serum chiral amino acids (D,L-Pro, D,L-Ser, and D,L-Ala).

The present invention relates to providing an accurate, minimally invasive method for diagnosing mild cognitive impairment or dementia, or a risk thereof.

The inventors found that mild cognitive impairment or dementia, or a risk thereof can be examined using the level of D-proline in the stereoisomer of proline in blood from patients with mild cognitive impairment and dementia as an indicator, and more accurate examinations can be performed by combining this with the levels of D-serine and D-alanine.

The method of the present invention enables mild cognitive impairment or dementia, or a risk thereof to be examined minimally invasively and conveniently and makes it easy and accurate to understand the change in cognitive decline at an early stage or intervene cognitive decline at an early stage.

In the present invention, "dementia" is a type of cognitive impairment and is a state in which the intelligence once normally developed is irreversibly degraded due to an acquired organic disorder of the brain. It is a disease usually caused by chronic or progressive brain disease and defined as a syndrome consisting of many disorders of higher cerebral functions such as memory, thinking, orientation, understanding, calculation, learning, language, and judgment.

Dementia is known to have types such as Alzheimer's disease, cerebrovascular dementia, Lewy body dementia, frontotemporal (pick type) dementia, juvenile dementia, mixed dementia, neurofibrillary tangles in senile dementia, argyrophilic grain dementia, frontotemporal lobar degeneration, progressive supranuclear palsy, corticobasal syndrome, posttraumatic syndrome after head injury, normal pressure hydrocephalus, alcoholic dementia, and chronic subdural hematoma. In the present invention, the type thereof is not limited as long as it exhibits the cognitive impairment but is preferably Alzheimer's disease, cerebrovascular dementia, Lewy body dementia, frontotemporal (pick type) dementia, and mixed dementia.

The "mild cognitive impairment" is called MCI and refers to a precursor state of dementia in which cognitive functions of the brain such as memory and attention are lower than normal but have not reached the level of dementia, or the earliest stage of dementia. It is a state defined as a pre-stage or borderline of various dementia in which there are problems in cognitive functions for age or as compared with normal aging, but there is no hindrance to daily life, and it is not yet determined to be dementia. For example, in the case where the score in the Mini Mental State Examination (MMSE) is 21 to 26 points, it is determined as MCI. It is said that MCI develops dementia with a high probability when left as it is and is considered to be in a state of having a risk of dementia.

In the present invention, the "examination" includes an examination for the presence or absence of dementia or mild cognitive impairment, an examination for the progression of symptoms of dementia or mild cognitive impairment, and an examination for the risk of dementia, preferably, an examination for the presence or absence of dementia or mild cognitive impairment. Here, the "examination for the risk" includes an examination for the likelihood of developing dementia in future. The "examination" includes the concept of "detection", "determination", or "diagnosis" but does not include medical practice such as diagnosis by a physician.

The method for examining mild cognitive impairment or dementia, or a risk thereof according to the present invention comprises the steps of: measuring the amount of stereoisomers of proline in a biological sample collected from a subject; and comparing the level of D-proline with a reference value.

The subject is not particularly limited in the present invention, but examples thereof include patients with subjective symptoms which characterize dementia or mild cognitive impairment such as memory impairment, disorientation, impairment of understanding or judgment, aphasia, agnosia, and apraxia, preferably, patients suspected of having dementia or mild cognitive impairment.

In the present invention, examples of the biological sample mainly include body fluids such as blood, lymph, saliva, and urine, preferably, a blood sample. Examples of the blood sample include blood (whole blood), serum derived from blood, and blood plasma, preferably, serum.

Blood can be collected from blood vessels of systemic circulation (such as arteries (peripheral arteries), veins (peripheral veins), and capillaries) or blood vessels of lung circulation (such as lung arteries, lung veins, and lung capillaries), but the blood is preferably collected from blood vessels, particularly, veins (peripheral veins) of systemic circulation, in view of ease of blood collection.

The amount of stereoisomers of proline in the biological sample may be measured by separating D-amino acids from L-amino acids in the biological sample, and technique thereof is not limited. Generally, a separation and quantification method using liquid chromatography (LC) and mass spectrometry (MS) in combination, such as LC-MS and LC-MS/MS can be employed. Here, a separation method using liquid chromatography in which an amino group is derivatized with AQC, and then a first chiral column having a stationary phase of weak anion exchange type and a second chiral column having a stationary phase of amphoteric ion exchange type are connected (JP-A-2018-100906) is known as a technique for separating chiral amino acids, for example, other than separation and quantification by two-dimensional liquid chromatography (LC) by converting an amino acid into an NBD derivative using a 4-fluoro-7-nitro-2,1,3-benzoxadiazol (NBD-F) reagent and then using a reverse phase column (first dimension: separation of molecular species) and a chiral column (second dimension: chiral separation) having a stationary phase carrying a chiral identifier (J Chromatogr A. 2010 Feb. 12; 1217(7):1056-62. doi: 10.1016/j.chroma.2009.09.002. Epub 2009 Sep. 6), one-dimensional LC using one reverse phase column (ODS column) (Anal Chim Acta. 2015 May 22; 875:73-82. doi: 10.1016/j.aca.2015.02.054. Epub 2015 Feb. 23), and one-dimensional LC by derivatizing an amino acid with 6-aminoquinolyl-N-hydroxysuccinimidyl carbamate (AQC) and using one chiral column (J Pharm Biomed Anal. 2015 Nov. 10; 115:123-9. doi: 10.1016/j.jpba.2015.05.024. Epub 2015 Jun. 16). It is preferably using the method of JP-A-2018-100906.

The level of D-proline may be the content or the composition value of D-proline but is preferably the chiral balance of proline of formula 1 below: {amount of D-proline/(amount of D-proline+amount of L-proline)}×100, that is, the D conversion rate of proline.

As shown later in Examples, it was observed that the chiral balance of proline had a good classification correlation with the MMSE score which is widely used as one of cognitive function examinations and was more excellent than the chiral balances of serine and alanine in that it had a good correlation with both dementia and mild cognitive impairment. When combining the chiral balance of proline and the chiral balance of serine, a better correlation was observed.

Accordingly, the presence or absence of mild cognitive impairment or dementia, and/or the risk of dementia can be evaluated by measuring at least the amount of stereoisomers of proline and comparing the level of D-proline with a reference value. Further, more detailed evaluation is enabled in evaluation obtained from the level of D-proline by measuring the amount of stereoisomers of serine and/or alanine in the same manner and appropriately combining the level of D-serine and/or D-alanine with the level of D-proline.

The level of D-serine is preferably the chiral balance of serine of formula 2 below: {amount of D-serine/(amount of D-serine+amount of L-serine)}×100, and the level of D-alanine is preferably the chiral balance of alanine of formula 3 below: {amount of D-alanine/(amount of D-alanine+amount of L-alanine)}×100.

The combination of the level of D-proline with the level of D-serine and/or D-alanine is, for example, preferably a product of these, specifically, the product of the chiral balances of proline and serine of formula 4 below: [{amount of D-proline/(amount of D-proline+amount of L-proline)}×100]×[{amount of D-serine/(amount of D-serine+amount of L-serine)}×100], the product of the chiral balances of proline and alanine of formula 5 below: [{amount of D-proline/(amount of D-proline+amount of L-proline)}×100]×[{amount of D-alanine/(amount of D-alanine+amount of L-alanine)}×100], or the product of the chiral balances of proline, serine, and alanine of formula 6 below: [{amount of D-proline/(amount of D-proline+amount of L-proline)}× 100]×[{amount of D-serine/(amount of D-serine+amount of L-serine)}×100]×[{amount of D-alanine/(amount of D-alanine+amount of L-alanine)}×100], preferably, the product of the chiral balances of proline and serine of formula 4.

In the present invention, the reference value for comparing the level of D-proline can be appropriately selected by those skilled in the art, and a pre-set cutoff value can be used, for example.

That is, in the case of using the chiral balance of proline or the product of the chiral balances of proline and serine and/or alanine as an indicator, it can be determined that dementia or mild cognitive impairment may be present and/or develop when the chiral balance of the same amino acid in the sample is greater than the pre-set cutoff value.

The cutoff value can be determined by various statistical analysis techniques. Examples thereof include the median or average in MMSE and a value based on ROC curve analysis (for example, Youden's index, the distance value from the upper left corner coordinates (0,1) in the ROC curve, or the like). It is also possible to set a plurality of cutoff values.

For example, in the case of using the chiral balance of proline of formula 1 as an indicator, when it is less than 0.38%, from 0.38% to 0.45%, or more than 0.45%, the subject is evaluated to be likely to be a healthy individual, an individual with mild cognitive impairment, or a dementia patient, respectively.

In the case of using the product of the chiral balances of proline and serine of formula 4 as an indicator, when it is less than 0.30%, from 0.30% to 0.50%, or more than 0.50%, the subject can be evaluated to be likely to be a healthy individual, an individual with mild cognitive impairment, or a dementia patient, respectively.

In the case of using the product of the chiral balances of proline and alanine of formula 5 as an indicator, when it is less than 0.20%, or 0.20% or more, the subject can be evaluated to be likely to be a healthy individual, or an individual with mild cognitive impairment or a dementia patient, respectively.

In the case of using the product of the chiral balances of proline, serine, and alanine of formula 6 as an indicator, when it is less than 0.20%, which may be 0.20% or more and increase up to about 0.50% with the progression of cognitive impairment, the subject can be evaluated to be likely to be a healthy individual, or an individual with mild cognitive impairment or a dementia patient, respectively. With further progression and onset of dementia, the value is between 0.35% and 0.20%. Accordingly, in the case of using the product of the chiral balances of proline, serine, and alanine as an indicator, when it is 0.20% or more, the subject can be evaluated to be likely to be an individual with mild cognitive impairment or a dementia patient, and the indicator can be used as an adjunct to other evaluation methods.

That is, the likelihood of being an individual with mild cognitive impairment or a dementia patient is determined by the evaluation using the chiral balance of proline of formula 1 as an indicator, and further evaluation that the likelihood is higher can be made when the same evaluation results are obtained by the evaluation using the chiral balances of formula 2 to formula 6 as indicators.

The present invention may be used in combination with other diagnosis of dementia than the present invention and enables multifaceted evaluation of mild cognitive impairment or dementia.

The apparatus for examining mild cognitive impairment or dementia, or a risk thereof according to the present invention is an apparatus for carrying out the aforementioned examination method of the present invention, comprising: a means for measuring the amount of stereoisomers of an amino acid in the biological sample; a means for comparing the level of D-amino acid with a reference value; and a means for outputting the condition of the subject or risk information thereof based on the comparison.

The means for measuring the amounts of stereoisomers of amino acids in the biological sample has an HPLC separation and peak detection unit using a reverse phase column or the like. The means for comparing the level of D-amino acid with a reference value has: a storage unit for storing data such as discriminants for determining the chiral balances and their products, and reference values of healthy persons, dementia patients, and persons with mild cognitive impairment; and a calculation unit for performing arithmetic processing based on the data. The means for outputting the condition or risk information thereof has a pathological condition information selection unit and a pathological condition information output unit. Other than above, a control unit such as CPU configured to generally control the whole, an input/output interface unit connected to an input device and an output device, and a communication interface unit communicably connected to the network are comprised therein.

Regarding the aforementioned embodiment, the following aspects are further disclosed in the present invention.

<1> A method for examining mild cognitive impairment or dementia, or a risk thereof, comprising the steps of: measuring the amount of stereoisomers of proline in a biological sample collected from a subject; and comparing the level of D-proline with a reference value.

<2> The method of <1>, wherein the level of D-proline is the chiral balance of proline of formula 1 below: {amount of D-proline/(amount of D-proline+amount of L-proline)}×100.

<3> The method of <2>, wherein when the chiral balance of proline of formula 1 is less than 0.38%, from 0.38% to 0.45%, or more than 0.45%, the subject is evaluated to be likely to be a healthy individual, an individual with mild cognitive impairment, or a dementia patient, respectively.

<4> The method of any one of <1> to <3>, further comprising the steps of: measuring the amount of stereoisomers of serine and/or alanine in the biological sample; and comparing a combination of the level of D-proline and the level of D-serine and/or D-alanine with a reference value.

<5> The method of <4>, wherein the level of D-serine is the chiral balance of serine of formula 2 below: {amount of D-serine/(amount of D-serine+amount of L-serine)}×100, and the level of D-alanine is the chiral balance of alanine of formula 3 below: {amount of D-alanine/(amount of D-alanine+amount of L-alanine)}×100.

<6> The method of <5>, wherein the combination of the level of D-proline and the level of D-serine and/or D-alanine is the product of the chiral balances of proline and serine of formula 4 below: [{amount of D-proline/(amount of D-proline+amount of L-proline)}×100]×{amount of D-serine/(amount of D-serine+amount of L-serine)}×100], the product of the chiral balances of proline and alanine of formula 5 below: [{amount of D-proline/(amount of D-proline+amount of L-proline)}×100]×[{amount of D-alanine/(amount of D-alanine+amount of L-alanine)}×100], or the product of the chiral balances of proline, serine, and alanine of formula 6 below: [{amount of D-proline/(amount of D-proline+amount of L-proline)}×100]×[{amount of D-serine/(amount of D-serine+amount of L-serine)}×100]×[{amount of D-alanine/(amount of D-alanine+amount of L-alanine)}×100].

<7> The method of <6>, wherein when the product of the chiral balances of proline and serine of formula 4 is less than 0.30%, from 0.30% to 0.50%, or more than 0.50%, the subject is evaluated to be likely to be a healthy individual, an individual with mild cognitive impairment, or a dementia patient, respectively.

<8> The method of <6>, wherein when the product of the chiral balances of proline and alanine of formula 5 is less than 0.20%, or 0.20 or more, the subject is evaluated to be likely to be a healthy individual, or an individual with mild cognitive impairment or a dementia patient, respectively.

<9> The method of <6>, wherein when the product of the chiral balances of proline, serine, and alanine of formula 6 is less than 0.20%, or 0.20% or more, the subject is evaluated to be likely to be a healthy individual, or an individual with mild cognitive impairment or a dementia patient, respectively.

<10> The method of any one of <1> to <9>, wherein the biological sample collected from the subject is a blood sample.

<11> An apparatus for performing the examination method of any one of <1> to <10> to examine mild cognitive impairment or dementia, or a risk thereof, comprising: a means for measuring the amount of stereoisomers of an amino acid in the biological sample; a means for comparing the level of D-amino acid with a reference value; and a means for outputting the condition of the subject or risk information thereof based on the comparison.

EXAMPLES

Hereinafter, the present invention will be described more specifically by way of examples.

Example 1: Simultaneous Separation Analyses of Chiral Amino Acids in Human Serum (1) Human Testing Analyses for the relationship between cognitive functions and blood components were performed on about 1,200 elderly women aged 65 and over living in Itabashi-ku, Tokyo. After collecting venous blood, serum was collected from each blood sample by centrifugation and stored frozen at −80° C. until the subsequent amino acid measurements. The Mini Mental State Examination (MMSE) was selected as the cognitive function evaluation method, and pre-trained testers listened individually.

The MMSE consists of a series of questions and tasks divided into 11 categories. That is, there are 11 categories of orientation regarding time, orientation regarding place, memorization, attention and calculation, reproduction, designation, repetition, understanding, reading, writing, and drawing. In most cases, the MMSE can be performed from 5 to 10 minutes. If all the questions are answered correctly, the maximum score of 30 points will be obtained. Performing and scoring the MMSE will be possible by those trained in conducting clinical interviews and behavioral measurements. Interpretation of the MMSE can be in an achievable region only by qualified professionals who have completed relevant learning tasks and training in cognitive mental condition assessment (refer to the MMSE-J user's guide, Nihon Bunka Kagakusha Co., Ltd.).

(2) Preparation of Sample Solution and Standard Product

50 µL of human serum was put into a 10 mL spitz glass (conical centrifuge tube) (product name: reinforced hard screw cap test tube), and 450 µL of a methanol:water (9:1, v/v) solution was mixed therein. Thereafter, centrifugation was performed at 3000 rpm in a centrifuge (CF5RE, available from Hitachi, Ltd.) at room temperature for 5 minutes for deproteinization, to collect amino acids in the supernatant. Then, a 0.2 mol/L borate buffer (pH 8.9), the solution collected, and an AccQ-Tag Ultra derivatization reagent, that is, AQC solution (available from Waters Corporation: AQC powder dissolved in acetonitrile at a concentration of 3 mg/mL, that is, 10 mmol/L) were mixed in amounts of 70 µL, 10 µL, and 20 µL (7:1:2), respectively, in this order in a 10 mL spitz glass (conical centrifuge tube). Immediately after stirring, a sample solution was prepared by heating at 55° C. for 10 minutes. Likewise, a 0.2 mol/L borate buffer (pH 8.9), a 100 µmol/L D,L-amino acid standard solution (amino acid: Ala/alanine, Arg/arginine, Asn/asparagine, Asp/aspartic acid, Cys/cysteine, Gln/glutamine, Glu/glutamic acid, Gly/glycine, His/histidine, Ile/isoleucine, Leu/leucine, Lys/lysine, Met/methionine, Phe/phenylalanine, Pro/proline, Ser/serine, Thr/threonine, Trp/tryptophan, Tyr/tyrosine, Val/valine, Cit/citrulline, or Orn/ornithine, dissolved in a 0.2 mol/L borate buffer), and an AQC solution were mixed in amounts of 70 µL, 10 µL, and 20 µL (7:1:2), respectively, in this order. Immediately after stirring, an amino acid standard solution was prepared by heating at 55° C. for 10 minutes.

(3) LC-MS/MS Analysis

The sample solution prepared in (2) was subjected to LC-MS/MS analysis under the following conditions, to perform separation detection and quantification of various chiral amino acids.

(Device)

Exion LC Series (available from AB SCIEX, LLC) Mass spectrometer: QTRAP6500$^+$ of linear ion trap type (available from AB SCIEX, LLC)

(Chromatography Separation)

Separation chiral columns: CHIRALPAK n-AX <Daicel Corporation> of 2.1 mm (inner diameter)×150 mm with a particle size of 5 µm (first chiral column) and CHIRALPAK ZWIX(+) <Daicel Corporation> of 3.0 mm (inner diameter)×150 mm with a particle size of 3 µm (second chiral column) connected in series in this order (45° C.)

Eluent: a methanol:water (90:10, v/v) solution containing 0.1% (v/v) formic acid and 55 mM ammonium formate Elution method: isocratic Flow rate of mobile phase: 0.25 mL/min Injection volume: 5 µL (Mass Spectrometry)

Ionization method: electrospray ionization (ESI)

Polarity: positive ion

Curtain Gas (CUR): 30 psi

Ionspray voltage (IS): 4500 V

Temperature (TEM): 600° C.

Ion Source Gas1 (GS1): 80 psi

Ion Source Gas1 (GS2): 80 psi

Collision Gas (CAD): 10

(Detection Mode)

SRM (selected reaction monitoring) detection by the positive ion mode with proton ion-added molecules ([M+H]$^+$) set as precursor ions and AQC fragment ions (m/z=171) set as product ions; and precursor ion scan detection by the positive ion mode with AQC fragment ions (m/z=171) set as product ions.

(4) Data Analysis

1) Analysis of Chiral Amino Acid

The data obtained in (3) was developed into a chromatogram having two axes of retention time and ionic strength, and various chiral amino acids after AQC derivatization (D,L-Pro, D,L-Ser, and D,L-Ala) in serum were analyzed. FIG. 1 shows typical chromatograms.

It turned out that none of them was affected by interfering components, and a trace amount of D-amino acid was detected in addition to L-amino acid. In serine and alanine, which are the primary amines, the D-form was eluted first, while in proline, which was the secondary amine, the L-form was eluted first.

Table 1 shows the SRM transition, with precursor ions set in Q1 (first stage MS) and product ions set in Q3 (second stage MS).

TABLE 1

| Molecular species | Q1 | Q3 |
|---|---|---|
| Lys | 487 | 171 |
| Orn | 473 | 171 |
| Trp | 375 | 171 |
| Tyr | 352 | 171 |
| Cit | 346 | 171 |
| Arg | 345 | 171 |
| Phe | 336 | 171 |
| His | 326 | 171 |
| Met | 320 | 171 |
| Glu | 318 | 171 |
| Gln | 317 | 171 |
| Asp | 304 | 171 |
| Asn | 303 | 171 |
| Ile | 302 | 171 |
| Leu | 302 | 171 |
| Cys | 292 | 171 |
| Thr | 290 | 171 |
| Val | 288 | 171 |
| Pro | 286 | 171 |
| Ser | 276 | 171 |
| Ala | 260 | 171 |
| Gly | 246 | 171 |

2) MMSE Score

Figure 2:
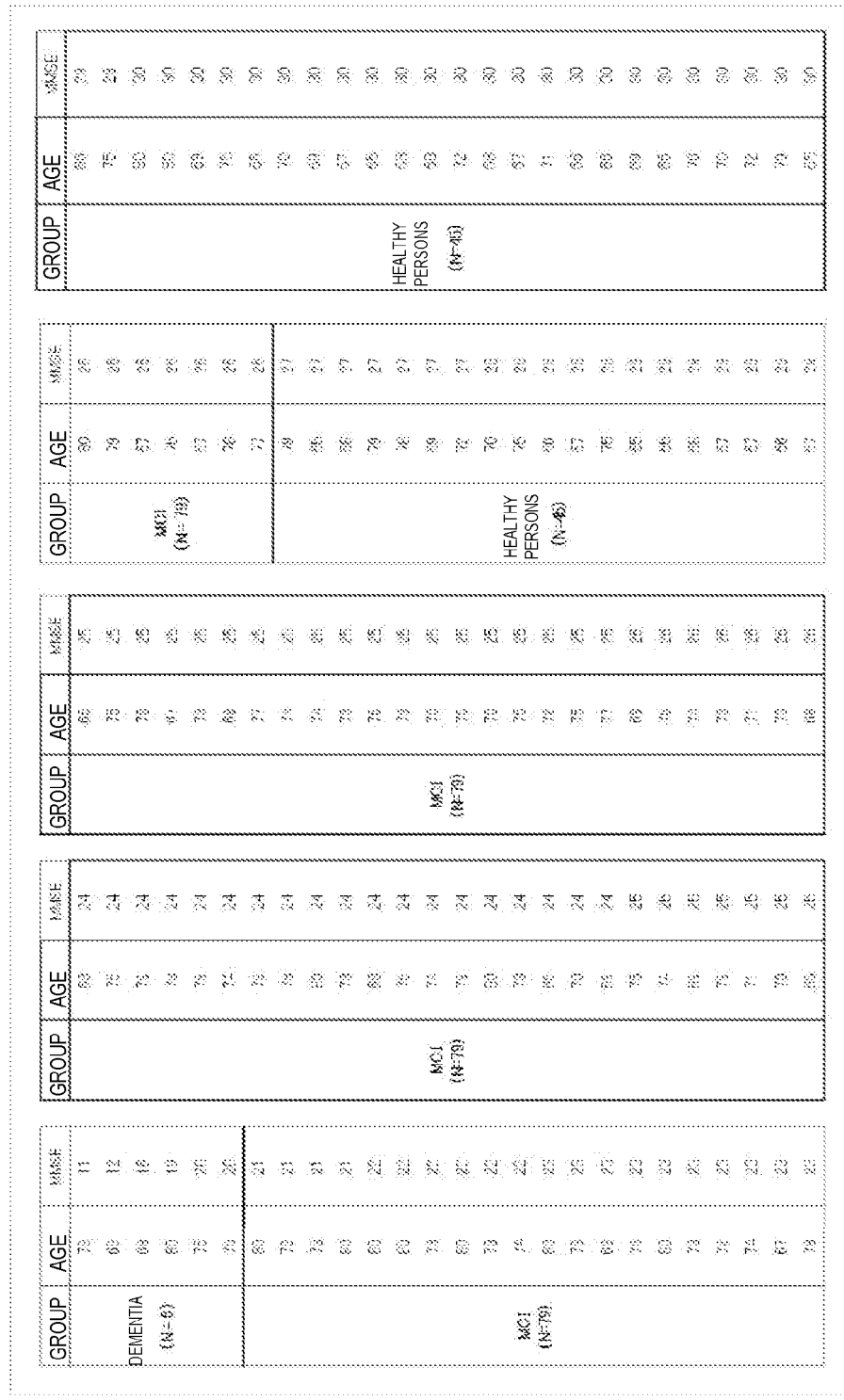
FIG. 2 shows age and MMSE scores of 130 subjects extracted.

FIG. 2 shows the ages and the MMSE scores of 130 subjects in total extracted at random from the target subjects. Those with normal cognitive functions (healthy persons) were classified as 27 to 30 points, those with mild cognitive impairment (MCI) as 21 to 26 points, and those suspected of dementia (dementia) as 20 points or less (refer to the MMSE-J user's guide, Nihon Bunka Kagakusha Co., Ltd.).

Figure 3:
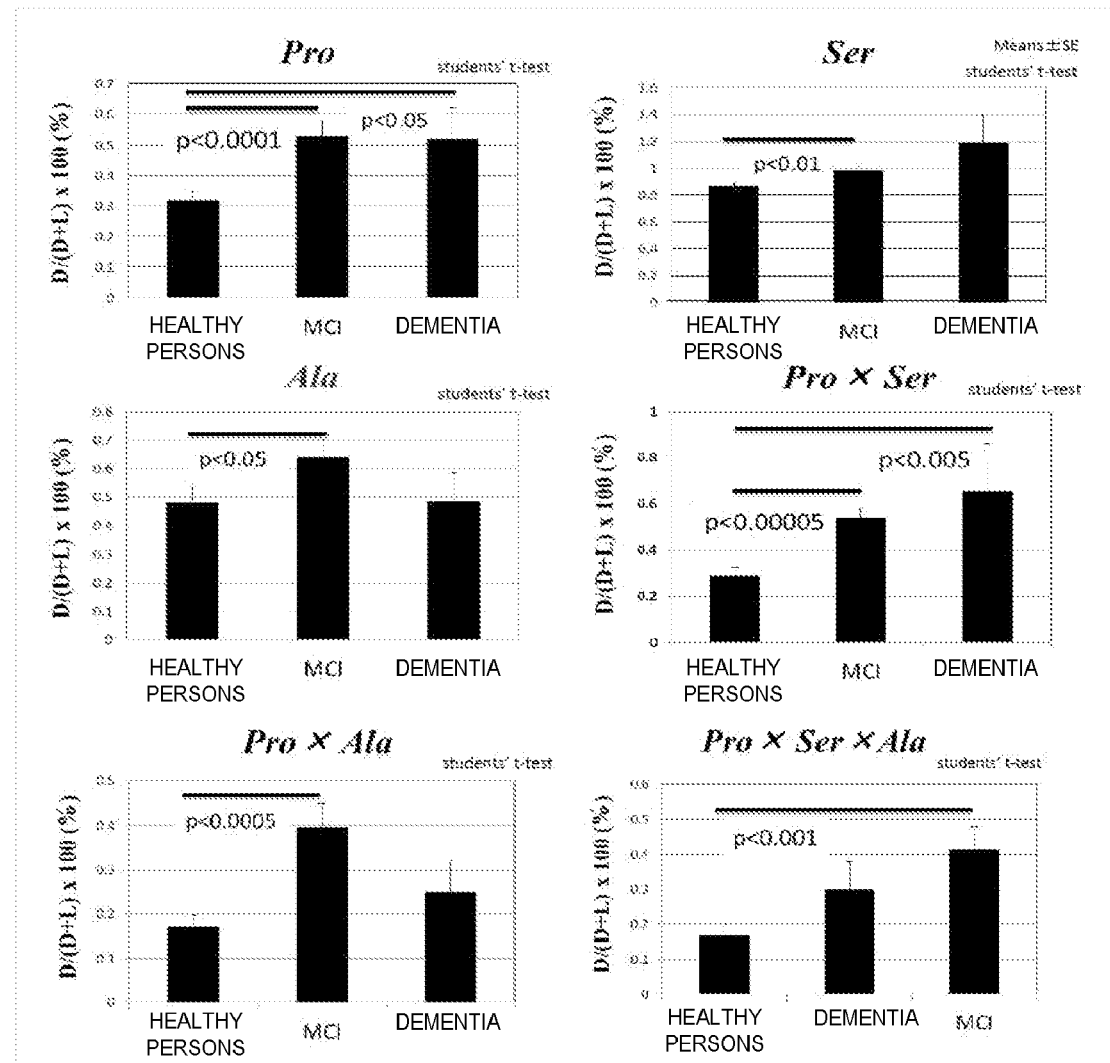
FIG. 3 shows the correlations between the chiral balances of serum D-amino acids (D-Pro, D-Ser, and D-Ala) and the MMSE scores.

3) Correlations Between Chiral Balances of Serum Chiral Amino Acids and MMSE Scores FIG. 3 shows correlations between the chiral balances (D conversion rates: D/(D+L)×100(%)) determined from the measured values of the amounts of serum chiral amino acids (Pro, Ser, and Ala) measured in (3) and their MMSE scores.

It turned out that the chiral balances of proline, serine, and alanine and their products correlate with the MMSE scores or the healthy, MCI, and dementia classification groups, confirming their involvement in cognitive functions. It was revealed that D-proline, D-serine, and D-alanine each showed a different profile. Particularly, it was confirmed that the chiral balance of proline or the product of the chiral balances of proline and serine strongly correlates with the MMSE and can be an indicator for the risk of early cognitive decline including the preclinical period.

(5) Usefulness Verification

Figure 4:
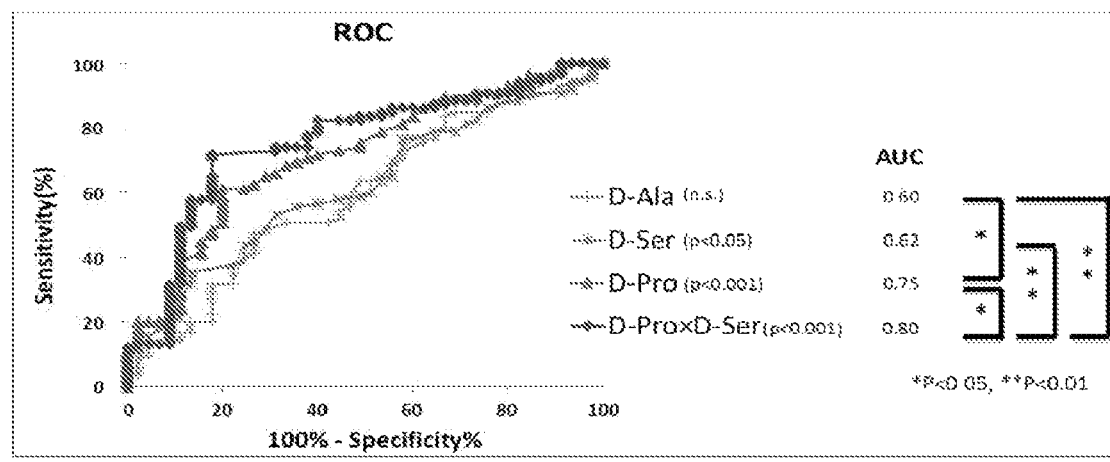
FIG. 4 shows a ROC curve in healthy vs. MCI.
Figure 5:
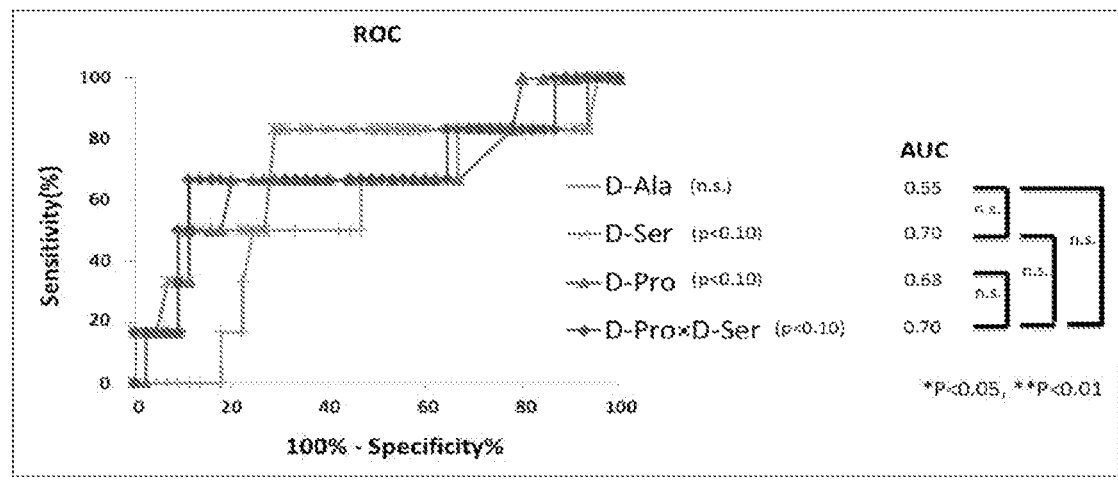
FIG. 5 shows a ROC curve in healthy vs. dementia.

Using Excel statistical processing software (BellCurve for Excel, available from Social Survey Research Information Co., Ltd.), a ROC (Receiver Operating Characteristic) curve is drawn, and the cutoff point (Cut off), the area under the ROC curve (AUC), the sensitivity (Sensitivity), and the specificity (Specificity) were each calculated. FIG. 4 shows the ROC curve for healthy vs. MCI, Table 2 shows the discrimination characteristics for healthy vs. MCI (Cut off, AUC, Sensitivity, and Specificity), FIG. 5 shows the ROC curve for healthy vs. dementia, and Table 3 shows the discrimination characteristics for healthy vs. dementia (Cut off, AUC, Sensitivity, and Specificity), respectively. In the test when the Cut off was set to the point closest to the upper left corner, and the null hypothesis was set to AUC=0.50, significant results were obtained when D-Pro was combined, and predictability was confirmed. When the AUC difference was tested, a difference in predictability was observed between the groups.

TABLE 2

| Combination | Cut off | AUC | Sensitivity | Specificity |
|---|---|---|---|---|
| D-Pro × D-Ser | 0.30 | 0.80 | 75% | 83% |
| D-Pro | 0.38 | 0.75 | 61% | 80% |
| D-Pro × D-Ser × D-Ala | 0.13 | 0.70 | 62% | 65% |
| D-Pro × D-Ala | 0.15 | 0.67 | 60% | 65% |

TABLE 3

| Combination | Cut off | AUC | Sensitivity | Specificity |
|---|---|---|---|---|
| D-Pro × D-Ser | 0.50 | 0.70 | 70% | 90% |
| D-Pro × D-Ser × D-Ala | 0.15 | 0.70 | 67% | 83% |
| D-Pro | 0.45 | 0.68 | 80% | 70% |
| D-Pro × D-Ala | 0.16 | 0.67 | 67% | 83% |

Example 2: Simultaneous Separation Analyses of Chiral Amino Acids in Human Serum in Longitudinal Cohort (1) Human Testing Longitudinal cohort analyses (in 2008, 2014, and 2018) of cognitive functions and blood components were performed on about 200 elderly women aged 75 and over living in Itabashi-ku, Tokyo. After collecting venous blood, serum was collected from each blood sample by centrifugation and stored frozen at −80° C. until the subsequent amino acid measurements. For the cognitive function evaluation method, the Mini Mental State Examination (MMSE) and the Mental Status Questionnaire (MSQ) were selected, and pre-trained testers listened individually.

(2) Preparation of Sample Solution and Standard Product

25 μL of human serum was put into a 10 mL spitz glass (conical centrifuge tube) (product name: reinforced hard screw cap test tube), and 475 μL of a methanol:water (9:1, v/v) solution was mixed therein. Thereafter, centrifugation was performed at 3000 rpm in a centrifuge (CFSRE, available from Hitachi, Ltd.) under refrigeration at 5° C. for 5 minutes for deproteinization, to collect amino acids in the supernatant. Then, a 0.2 mol/L borate buffer (pH 8.9), the solution collected, and an AccQ-Tag Ultra derivatization reagent, that is, AQC solution (available from Waters Corporation: AQC powder dissolved in acetonitrile at a concentration of 3 mg/mL, that is, 10 mmol/L) were mixed in amounts of 70 μL, 10 μL, and 20 μL (7:1:2), respectively, in this order in a 10 mL spitz glass (conical centrifuge tube). Immediately after stirring, a sample solution was prepared by heating at 55° C. for 10 minutes. Likewise, a 0.2 mol/L borate buffer (pH 8.9), a 100 μmol/L D,L-amino acid standard solution (amino acid: Ala/alanine, Arg/arginine, Asn/asparagine, Asp/aspartic acid, Cys/cysteine, Gln/glutamine, Glu/glutamic acid, Gly/glycine, His/histidine, Ile/isoleucine, Leu/leucine, Lys/lysine, Met/methionine, Phe/phenylalanine, Pro/proline, Ser/serine, Thr/threonine, Trp/tryptophan, Tyr/tyrosine, Val/valine, Cit/citrulline, or Orn/ornithine, dissolved in a 0.2 mol/L borate buffer), and an AQC solution were mixed in amounts of 70 μL, 10 μL, and 20 μL (7:1:2), respectively, in this order.

Immediately after stirring, an amino acid standard solution was prepared by heating at 55° C. for 10 minutes.

(3) LC-MS/MS Analysis

In the same manner as in Example 1, the sample solution prepared in (2) was subjected to LC-MS/MS analysis under the following conditions, to perform separation detection and quantification of various chiral amino acids.

(Device)
Exion LC Series (available from AB SCIEX, LLC)
Mass spectrometer: QTRAP6500$^+$ of linear ion trap type (available from AB SCIEX, LLC)
(Chromatography Separation)
Separation chiral columns: CHIRALPAK QN-AX <Daicel Corporation> of 2.1 mm (inner diameter)×150 mm with a particle size of 5 μm (first chiral column) and CHIRALPAK ZWIX(+) <Daicel Corporation> of 3.0 mm (inner diameter)×150 mm with a particle size of 3 μm (second chiral column) connected in series in this order (45° C.)
Eluent: a methanol:water (90:10, v/v) solution containing 0.1% (v/v) formic acid and 55 mM ammonium formate
Elution method: isocratic
Flow rate of mobile phase: 0.25 mL/min
Injection volume: 5 μL
(Mass Spectrometry)
Ionization method: electrospray ionization (ESI)
Polarity: positive ion
Curtain Gas (CUR): 30 psi
Ionspray voltage (IS): 4500 V
Temperature (TEM): 600° C.
Ion Source Gas1 (GS1): 80 psi
Ion Source Gas1 (GS2): 80 psi
Collision Gas (CAD): 10 (detection mode)
SRM (selected reaction monitoring) detection by the positive ion mode with proton ion-added molecules ([M+H]$^+$) set as precursor ions and AQC fragment ions (m/z=171) set as product ions; and precursor ion scan detection by the positive ion mode with AQC fragment ions (m/z=171) set as product ions.

(4) Data Analysis
1) Analysis of Chiral Amino Acid

In the same manner as in Example 1, the data obtained in (3) was developed into a chromatogram having two axes of retention time and ionic strength, and various chiral amino acids after AQC derivatization (D,L-Pro and D,L-Ser) were analyzed.

Figure 6:
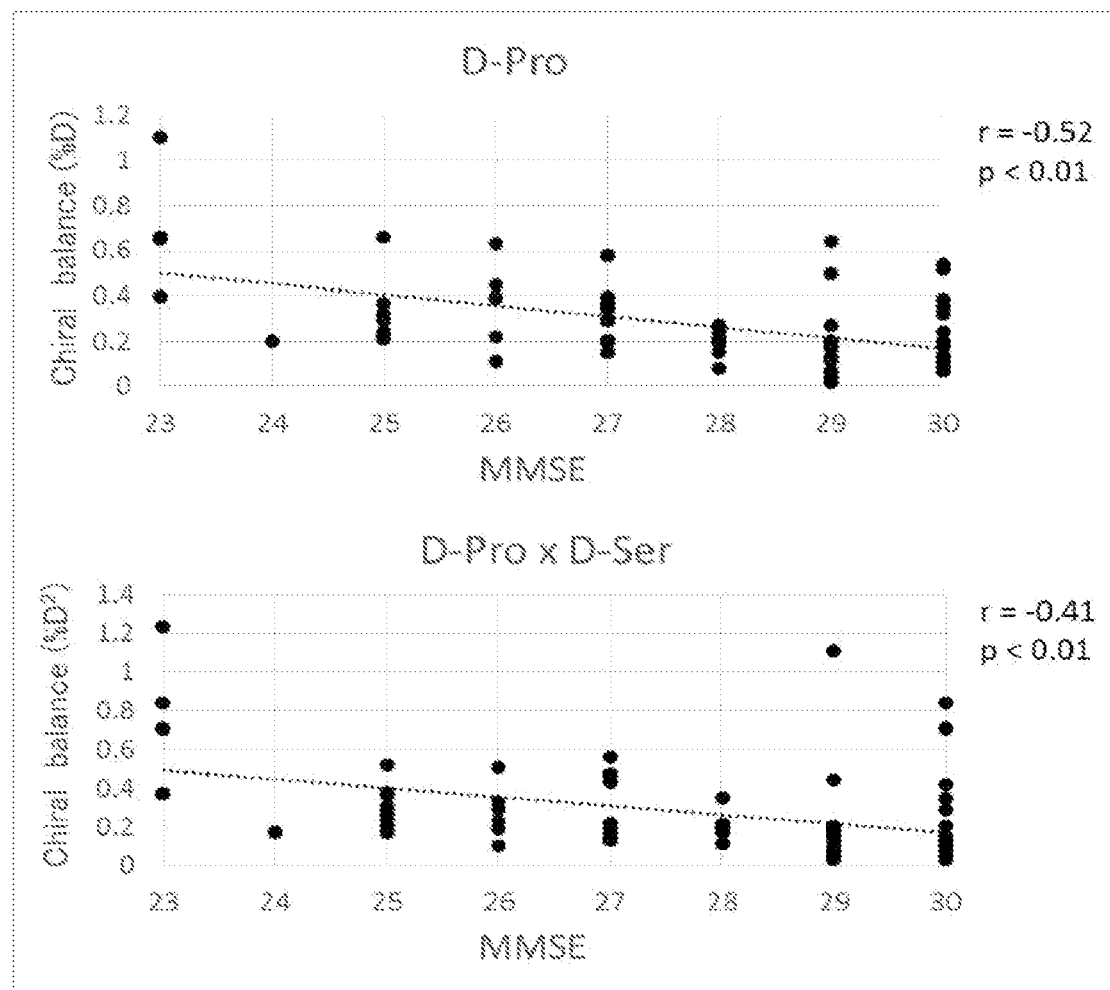
FIG. 6 shows the correlations between the chiral balances of serum D-amino acids (D-Pro and D-Pro×D-Ser) in longitudinal cohort analysis and the MMSE scores.
Figure 7:
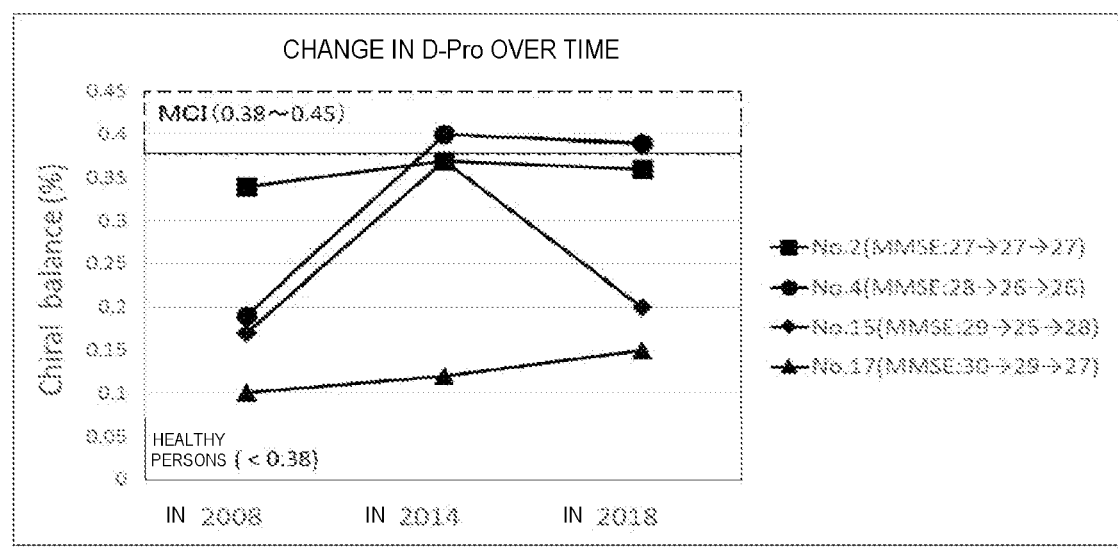
FIG. 7 shows the relationship between the MMSE and the change in D-Pro over time.

2) Correlations Between Chiral Balances of Serum Chiral Amino Acids and MMSE Scores Table 4, FIG. 6, and FIG. 7 show the relationships between the MMSE scores of 23 subjects extracted at random from the target subjects for each year and the chiral balances determined from the measured values of the amounts of serum chiral amino acids (D,L-Pro and D,L-Ser) measured in (3).

TABLE 4

|  | MMSE | | | D-Pro | | | D-Pro × D-Ser | | |
| --- | --- | --- | --- | --- | --- | --- | --- | --- | --- |
|  | 2008 | 2014 | 2018 | 2008 | 2014 | 2018 | 2008 | 2014 | 2018 |
| No. 1 | 29 | 26 | 29 | 0.07 | 0.11 | 0.02 | 0.05 | 0.10 | 0.03 |
| No. 2 | 27 | 27 | 27 | 0.34 | 0.37 | 0.36 | 0.47 | 0.43 | 0.47 |
| No. 3 | 27 | 25 | 26 | 0.40 | 0.66 | 0.45 | 0.22 | 0.52 | 0.33 |
| No. 4 | 28 | 26 | 26 | 0.19 | 0.40 | 0.39 | 0.20 | 0.29 | 0.23 |
| No. 5 | 27 | 23 | 23 | 0.53 | 1.10 | 0.55 | 0.56 | 1.23 | 0.84 |
| No. 6 | 30 | 29 | 30 | 0.12 | 0.50 | 0.35 | 0.10 | 0.44 | 0.35 |
| No. 7 | 30 | 26 | 30 | 0.24 | 0.63 | 0.39 | 0.29 | 0.51 | 0.42 |
| No. 8 | 28 | 25 | 28 | 0.15 | 0.24 | 0.21 | 0.11 | 0.38 | 0.35 |
| No. 9 | 30 | 29 | 30 | 0.14 | 0.27 | 0.07 | 0.12 | 0.20 | 0.03 |
| No. 10 | 25 | 26 | 29 | 0.22 | 0.22 | 0.12 | 0.27 | 0.19 | 0.07 |
| No. 11 | 30 | 30 | 30 | 0.10 | 0.11 | 0.07 | 0.10 | 0.09 | 0.05 |
| No. 12 | 29 | 28 | 25 | 0.20 | 0.21 | 0.23 | 0.17 | 0.21 | 0.30 |
| No. 13 | 30 | 27 | 28 | 0.12 | 0.29 | 0.27 | 0.10 | 0.19 | 0.17 |
| No. 14 | 28 | 24 | 29 | 0.08 | 0.20 | 0.04 | 0.11 | 0.17 | 0.04 |
| No. 15 | 29 | 25 | 28 | 0.17 | 0.37 | 0.20 | 0.19 | 0.36 | 0.20 |
| No. 16 | 30 | 29 | 30 | 0.52 | 0.64 | 0.54 | 0.71 | 1.11 | 0.84 |
| No. 17 | 30 | 29 | 27 | 0.10 | 0.12 | 0.15 | 0.08 | 0.08 | 0.13 |
| No. 18 | 29 | 25 | 30 | 0.13 | 0.32 | 0.07 | 0.16 | 0.24 | 0.04 |
| No. 19 | 30 | 23 | 23 | 0.32 | 0.66 | 0.40 | 0.20 | 0.71 | 0.37 |
| No. 20 | 30 | 25 | 27 | 0.13 | 0.21 | 0.20 | 0.12 | 0.17 | 0.13 |
| No. 21 | 30 | 30 | 28 | 0.19 | 0.18 | 0.24 | 0.14 | 0.14 | 0.19 |
| No. 22 | 30 | 29 | 25 | 0.20 | 0.17 | 0.29 | 0.15 | 0.14 | 0.20 |
| No. 23 | 29 | 30 | 27 | 0.19 | 0.07 | 0.20 | 0.11 | 0.05 | 0.16 |

It turned out that the Pro-related indices (Pro-single chiral balance or multi-chiral balances of Pro and Ser) had significant negative correlations with the MMSE scores not only in the cross-sectional study but also in the longitudinal study (FIG. 6), and usefulness for evaluation of cognitive functions was again confirmed (those with cognitive decline had a high chiral balance). In addition, it turned out that evaluation of effects of treatment, intervention or the like is also possible for each individual as well as serving as indices for evaluating healthy persons or the state of mild cognitive impairment or dementia (FIG. 7). For example, it was found that evaluation of recovery of MMSE, that is, recovery of cognitive functions and prediction of prognosis can be performed, so that those with constant MMSE had a constant chiral balance (No. 2), and those with fluctuations in MMSE also had fluctuations in chiral balance (No. 15). Usefulness for monitoring cognitive functions was found.

The invention claimed is:

1. A method for examining mild cognitive impairment or dementia, or a risk thereof, the method comprising:
    measuring an amount of stereoisomers of proline in a biological sample collected from a subject; and
    comparing a level of D-proline with a reference value,
    wherein the level of D-proline is a chiral balance of proline of formula 1 below:

{amount of D-proline/(amount of D-proline+amount of L-proline)}×100, and wherein when the chiral balance of proline of formula 1 is less than 0.38%, from 0.38% to 0.45%, or more than 0.45%, the subject is evaluated as likely to be a healthy individual, an individual with mild cognitive impairment, or a dementia patient, respectively.

2. The method according to claim 1, further comprising:
    measuring an amount of stereoisomers of serine and/or alanine in the biological sample; and
    comparing a combination of the level of D-proline and a level of D-serine and/or D-alanine with a reference value.

3. The method according to claim 2, wherein the level of D-serine is a chiral balance of serine of formula 2 below:

{amount of D-serine/(amount of D-serine+amount of L-serine)}×100, and the level of D-alanine is a chiral balance of alanine of formula 3 below:

{amount of D-alanine/(amount of D-alanine+amount of L-alanine)}×100.

4. The method according to claim 3, wherein the combination of the level of D-proline and the level of D-serine and/or D-alanine is a product of chiral balances of proline and serine of formula 4 below:

[{amount of D-proline/(amount of D-proline+amount of L-proline)}×100]×{amount of D-serine/(amount of D-serine+amount of L-serine)}×100], a product of chiral balances of proline and alanine of formula 5 below: [{amount of D-proline/(amount of D-proline+amount of L-proline)}×100]×[{amount of D-alanine/(amount of D-alanine+amount of L-alanine)}×100], or a product of the chiral balances of proline, serine, and alanine of formula 6 below:

[{amount of D-proline/(amount of D-proline+amount of L-proline)}×100]×[{amount of D-serine/(amount of D-serine+amount of L-serine)}×100]×[{amount of D-alanine/(amount of D-alanine+amount of L-alanine)}×100].

5. The method according to claim 4, wherein when the product of the chiral balances of proline and serine of formula 4 is less than 0.30%, from 0.30% to 0.50%, or more than 0.50%, the subject is evaluated as likely to be a healthy individual, an individual with mild cognitive impairment, or a dementia patient, respectively.

6. The method according to claim 4, wherein when the product of the chiral balances of proline and alanine of formula 5 is less than 0.20%, or 0.20% or more, the subject is evaluated as likely to be a healthy individual, or an individual with mild cognitive impairment or a dementia patient, respectively.

7. The method according to claim 4, wherein when the product of the chiral balances of proline, serine, and alanine of formula 6 is less than 0.20%, or 0.20% or more, the subject is evaluated as likely to be a healthy individual, or an individual with mild cognitive impairment or a dementia patient, respectively.

8. The method according to claim 1, wherein the biological sample collected from the subject is a blood sample.

* * * * *